United States Patent [19]
Monia et al.

[11] Patent Number: 6,133,031
[45] Date of Patent: Oct. 17, 2000

[54] ANTISENSE INHIBITION OF FOCAL ADHESION KINASE EXPRESSION

[75] Inventors: Brett P. Monia, LaCosta; William A. Gaarde, Carlsbad, both of Calif.

[73] Assignee: Isis Pharmaceuticals Inc., Carlsbad, Calif.

[21] Appl. No.: 09/377,310

[22] Filed: Aug. 19, 1999

[51] Int. Cl.[7] .............................. C07H 21/04; C12Q 1/68; C12N 15/00
[52] U.S. Cl. .............................. 435/375; 435/6; 435/91.1; 536/23.1; 536/24.5; 514/44
[58] Field of Search .............................. 435/6, 91.1, 91.3, 435/375, 325; 536/23.1, 23.2, 24.5, 24.3, 24.31, 24.33; 514/44

[56] References Cited

U.S. PATENT DOCUMENTS 6,015,893  1/2000  Cance et al. .............................. 536/24.5

OTHER PUBLICATIONS

Lou, et al., "In Vivo Gene Transfer and Overexpression of Focal Adhesion Kinase (pp125 FAK) Mediated by Recombinant Adenovirus–Induced Tendon Adhesion Formation and Epitenon Cell Change", *J. Orthopaedic Res.* 1997, 15, 911–918.

Naruse, et al., "Pp125$^{FAK}$ is required for stretch dependent morphological response of endothelial cells", *Oncogene* 1998, 17, 445–463.

Shibata, K., et al., "Both Focal Adhesion Kinase and c–Ras Are Required for the Enhanced Matrix Metalloproteinase 9 Secretion by Fibronectin in Ovarian Cancer Cells[1]", *Cancer Res.*, 1998, 5, 900–903.

Sonoda, et al., "A Suppressive Role of p125FAK Protein Tyrosine Kinase in Hydrogen Peroxide–Induced Apoptosis of T98G Cells", *Biochem. Biophys. Res. Comm.*, 1997, 241, 769–774.

Tanaka et al., "Possible Involvement of Focal Adhesion Kinase, p125$^{FAK}$, in Osteoclastic Bone Resorption", *J. Cell. Biochem.* 1995, 58, 424–435.

Takeuchi, et al., "Differentiation and Transforming Growth Factor–β Receptor Down–regulation by Collagen–α2β1 Integrin Interaction Is Mediated by Focal Adhesion Kinase and Its Downstream Signals in Murine Osteoblastic Cells", *J. Biol. Chem.*, 1997, 272, 29309–29316.

Xu, et al., "Attenuation of the Expression of the Focal Adhesion Kinase Induces Apoptosis in Tumor Cells[1]", *Cell Growth Diff.*, 1996, 7, 413–418.

*Primary Examiner*—George C. Elliott
*Assistant Examiner*—Karen A Lacourciere
*Attorney, Agent, or Firm*—Law Offices of Jane Massey Licata

[57] ABSTRACT

Compounds, compositions and methods are provided for inhibiting FAK mediated signaling. The compositions comprise antisense compounds targeted to nucleic acids encoding FAK. Methods of using these antisense compounds for inhibition of FAK expression and for treatment of diseases, particularly cancers, associated with overexpression or constitutive activation of FAK are provided.

29 Claims, No Drawings

ANTISENSE INHIBITION OF FOCAL ADHESION KINASE EXPRESSION

FIELD OF THE INVENTION

This invention relates to compositions and methods for modulating expression of the human focal adhesion kinase (FAK) gene, which encodes a signaling protein involved in growth factor response and cell migration and is implicated in disease. This invention is also directed to methods for inhibiting FAK-mediated signal transduction; these methods can be used diagnostically or therapeutically. Furthermore, this invention is directed to treatment of conditions associated with expression of the human FAK gene.

BACKGROUND OF THE INVENTION

Cell migration is fundamental to a variety of biological processes and can be induced by both integrin receptor-mediated signals (haptotaxis migration) and/or soluble growth factor-mediated signals (chemotaxis migration). Integrin receptor engagement activates focal adhesion kinase (FAK, also pp125FAK), a non-receptor protein-tyrosine kinase localized to cell substratum-extracellular matrix (ECM) contact sites that function as part of a cytoskeletal-associated network of signaling proteins (Schlaepfer, D. D., et al., *Prog. Biophys. Mol. Biol.,* 1999, 71, 435–478). In adherent cells, FAK is often associated with integrins at focal adhesions (Schaller, M. D., et al., *Proc. Natl. Acad. Sci. USA,* 1992, 89, 5192–5196). Numerous other signaling proteins, including other protein tyrosine kinases are associated with FAK at these regions. Phosphorylation of FAK results in activation of the mitogen-activated protein kinase pathway. In addition, FAK regulates activation of phosphatidylinositol 3'-kinase which may serve to prevent apoptosis. FAK has also been shown to be required for internalization of bacteria mediated by invasin (Alrutz, M. A. and Isberg, R. R., *Proc. Natl. Acad. Sci. USA,* 1998, 95, 13658–13663).

Normal cells typically require anchorage to the extracellular matrix in order to grow. When these cells are removed from the extracellular matrix, they undergo apoptosis. Transformed cells, on the other hand, can grow under anchorage-independent conditions, providing them a growth advantage and the ability to be removed from their normal cellular environment.

Overexpression of FAK is involved in cancer progression. High levels of FAK correlates with invasiveness and metastatic potential in colon tumors (Weiner, T. M., et al., *Lancet,* 1993, 342, 1024–1025), breast tumors (Owens, L. V., et al., *Cancer Res.,* 1995, 55, 2752–2755), and oral cancers (Kornberg, L. J., *Head Neck,* 1998, 20, 634–639).

FAK's role in cell migration has led to the speculation that it may be relevant in other diseases such as embryonic development disfunctions and angiogenic disorders (Kornberg, L. J., *Head Neck,* 1998, 20, 634–639).

There is a lack of specific inhibitors of FAK. Antisense approaches have been a means by which the function of FAK has been investigated. Lou, J. et al. (*J. Orthopaedic Res.,* 1997, 15, 911–918) used an adenoviral based vector to express antisense FAK RNA to show that FAK is involved in wound healing in tendons. Another antisense FAK expression vector containing 400 bp of complementary sequence was used to study the interaction of type I collagen and α2β1 integrin (Takeuchi, Y., et al., *J. Biol. Chem.,* 1997, 272, 29309–30 29316).

Antisense oligonucleotides have been used in several studies. Tanaka, S. et al. (*J. Cell. Biochem.,* 1995, 58, 424–435) disclose two antisense phosphorothioate oligonucleotides targeted to the start site of mouse FAK. Xu, L. -H., et al. (*Cell Growth Diff.,* 1996, 7, 413–418) disclose two antisense phosphorothioate oligonucleotides targeted within the coding region of human FAK. They also show that FAK antisense treatment could induce apoptosis in tumor cells. Sonoda, Y., et al. (*Biochem. Biophys. Res. Comm.,* 1997, 241, 769–774) also demonstrated a role for FAK in apoptosis using antisense phosphorothioate oligonucleotides targeted to the start site and within the coding region of human FAK. Shibata, K., et al. (*Cancer Res.,* 1998, 58, 900–903) disclose antisense phosphorothioate oligonucleotides targeted to the start site and coding region of human FAK. Narase, K., et al. (*Oncogene,* 1998, 17, 455–463) disclose an antisense phosphorothioate oligonucleotide targeted to the start site of human FAK.

There remains a long-felt need for improved compositions and methods for inhibiting FAK gene expression.

SUMMARY OF THE INVENTION

The present invention provides antisense compounds which are targeted to nucleic acids encoding focal adhesion kinase expression (FAK) and are capable of modulating FAK mediated signaling. The present invention also provides chimeric oligonucleotides targeted to nucleic acids encoding human FAK. The antisense compounds of the invention are believed to be useful both diagnostically and therapeutically, and are believed to be particularly useful in the methods of the present invention.

The present invention also comprises methods of modulating FAK mediated signaling, in cells and tissues, using the antisense compounds of the invention. Methods of inhibiting FAK expression are provided; these methods are believed to be useful both therapeutically and diagnostically. These methods are also useful as tools, for example, for detecting and determining the role of FAK in various cell functions and physiological processes and conditions and for diagnosing conditions associated with expression of FAK.

The present invention also comprises methods for diagnosing and treating cancers, including those of the colon, breast and mouth. These methods are believed to be useful, for example, in diagnosing FAK-associated disease progression. These methods employ the antisense compounds of the invention. These methods are believed to be useful both therapeutically, including prophylactically, and as clinical research and diagnostic tools.

DETAILED DESCRIPTION OF THE INVENTION

FAK plays important roles in integrin-mediated signal transduction. Overexpression of FAK is associated with tumor progression and metastatic potential. As such, this protein represents an attractive target for treatment of such diseases. In particular, modulation of the expression of FAK may be useful for the treatment of diseases such as colon cancer, breast cancer and cancer of the mouth.

The present invention employs antisense compounds, particularly oligonucleotides, for use in modulating the function of nucleic acid molecules encoding FAK, ultimately modulating the amount of FAK produced. This is accomplished by providing oligonucleotides which specifically hybridize with nucleic acids, preferably mRNA, encoding FAK.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the targets are nucleic acids encoding FAK; in other words, a gene encoding FAK, or mRNA expressed from the FAK gene. mRNA which encodes FAK is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding FAK, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of FAK. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently preferred.

The oligonucleotides of this invention can be used in diagnostics, therapeutics, prophylaxis, and as research reagents and in kits. Since the oligonucleotides of this invention hybridize to nucleic acids encoding FAK, sandwich, calorimetric and other assays can easily be constructed to exploit this fact. Provision of means for detecting hybridization of oligonucleotide with the FAK genes or mRNA can routinely be accomplished. Such provision may include enzyme conjugation, radiolabelling or any other suitable detection systems. Kits for detecting the presence or absence of FAK may also be prepared.

The present invention is also suitable for diagnosing abnormal inflammatory states or certain cancers in tissue or other samples from patients suspected of having an autoimmune or inflammatory disease such as hepatitis or cancers such as those of the colon, liver or lung, and lymphomas. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide (s), usually in a liquid carrier, to a cell suspension or tissue sample, either in vitro or ex vivo, or to administer the oligonucleotide(s) to cells or tissues within an animal.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al. (*Science*, 1991, 254, 1497–1500).

Most preferred embodiments of the invention are oligonucleotides with phosphorothioate backbones and oligonucleosides with heteroatom backbones, and in particular —$CH_2$—NH—O—$CH_2$—, —CH—$_2$N(CH)$_3$—O—CH—$_2$ [known as a methylene (methylimino) or MMI backbone], —$CH_2$—O—N($CH_3$)—$CH_2$-,—$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl, O-alkyl-O-alkyl, O—, S—, or N-alkenyl, or O—, S— or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_2$ON($CH_3$)$_2$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'—O—$CH_2CH_2OCH_3$, also known as 2'—O—(2-methoxyethyl) or 2'-MOE) (Martin et al., *Helv. Chim. Acta* 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, and 2'-dimethylaminoethoxyethoxy (2'-DMAEOE), i.e., 2'—O—$CH_2$—O—$CH_2$—N($CH_2$)$_2$.

Other preferred modifications include 2'-methoxy (2'—O—$CH_3$), 2'-aminopropoxy (2'—O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-amincadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6 -azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering 1990, pages 858–859, Kroschwitz, J. I., ed. John Wiley & Sons, those disclosed by Englisch et al. (*Angewandte Chemie*, International Edition 1991, 30, 613–722), and those disclosed by Sanghvi, Y. S., Chapter 15, *Antisense Research and Applications* 1993, pages 289–302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, CRC Press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA* 1989, 86, 6553–6556), cholic acid (Manoharan et al., *Bioorg. Med. Chem. Lett.* 1994, 4, 1053–1059), a thioether, e.g., hexyl-S-tritylthiol (Manoharan et al., *Ann. N.Y. Acad. Sci.* 1992, 660, 306–309; Manoharan et al., *Bioorg. Med. Chem. Let.* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.* 1991, 10, 1111–1118; Kabanov et al., *FEBS Lett.* 1990, 259, 327–330; Svinarchuk et al., *Biochimie* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 1995, 36, 3651–3654; Shea et al., *Nucl. Acids Res.* 1990, 18, 3777–3783), a polyamine or a polyethylene glycol chain (Manoharan et al., *Nucleosides & Nucleotides* 1995, 14, 969–973), or adamantane acetic acid (Manoharan et al., *Tetrahedron Lett.* 1995, 36, 3651–3654), a palmityl moiety (Mishra et al., *Biochim. Biophys. Acta* 1995, 1264, 229–237), or an octadecylamine or hexylamino-carbonyl-oxycholesterol moiety (Crooke et al., *J. Pharmacol. Exp. Ther.* 1996, 277, 923–937).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'—O—CH$_2$CH$_2$OCH$_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—CH$_2$CH$_2$OCH$_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 21-O-methoxyethyl modifications, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 21-alkoxyalkoxy derivatives, including 2'-O-methoxyethyl oligonucleotides (Martin, P., *Helv. Chim. Acta* 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. "Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.* 1977, 66, 1–19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems* 1991, 8, 91–192; Muranishi, *Critical Reviews in Therapeutic Drug Carrier Systems* 1990, 7, 1–33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. Pharmacol.* 1992 44, 651–654).

The physiological roles of bile include the facilitation of dispersion and absorption of lipids and fat-soluble vitamins (Brunton, Chapter 38 In: *Goodman & Gilman's The Pharmacological Basis of Therapeutics,* 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)[Lee et al., *Critical Reviews in Therapeutic Drug Carrier Systems* 1991, page 92; Muranishi, *Critical Reviews in Therapeutic Drug Carrier Systems* 1990, 7, 1–33; Buur et al., *J. Control Rel.* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. Phamacol.* 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems* 1991, page 92); and non-steroidal anti-inflammatory agents such as diclofenac sodium, indomethacin and phenylbutazone (Yamashita et al., *J. Pharm. Pharmacol.* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. I n contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698–708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, *The Merck Manual of Diagnosis and Therapy,* 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The following examples illustrate the present invention and are not intended to limit the same.

EXAMPLES

Example 1

Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step. Cytosines may be 5-methyl cytosines. (5-methyl deoxycytidine phosphoramidites available from Glen Research, Sterling, Va. or Amersham Pharmacia Biotech, Piscataway, N.J.)

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va.

2'-fluoro oligonucleotides are synthesized as described in Kawasaki et al. (*J. Med. Chem.* 1993, 36, 831–841). Briefly, the protected nucleoside $N^6$-benzoyl-2'-deoxy-2'-fluoroadenosine is synthesized utilizing commercially available 9-β-D-arabinofuranosyladenine as starting material and by modifying literature procedures whereby the $2^1$-α-fluoro atom is introduced by a $S_N2$-displacement of a 2'-β-O-trifyl group. Thus $N^6$-benzoyl-9-β-D-arabinofuranosyladenine is selectively protected in moderate yield as the 3',5'-ditetrahydropyranyl (THP) intermediate. Deprotection of the THP and $N^6$-benzoyl groups is accomplished using standard methodologies and standard methods are used to obtain the 5'-dimethoxytrityl-(DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2,2'-anhydro-1-β-D-arabinofuranosyluracil is treated with 70% hydrogen fluoride-pyridine. Standard procedures are used to obtain the 5'-DMT and 5'-DMT-3'phosphoramidites.

2'-deoxy-2'-fluorocytidine is synthesized via amination of 2'-deoxy-2'-fluorouridine, followed by selective protection to give $N^4$-benzoyl-2'-deoxy-2'-fluorocytidine. Standard procedures are used to obtain the 5'-DMT and 5'-DMT-3'phosphoramidites.

2'-(2-methoxyethyl)-modified amidites were synthesized according to Martin, P. (Helv. *Chim. Acta* 1995, 78, 486–506). For ease of synthesis, the last nucleotide may be a deoxynucleotide. 2'—O—$CH_2CH_2CH_3$cytosines may be 5-methyl cytosines.

Synthesis of 5-Methyl cytosine monomers:

2,2'-Anhydro [1-(β-D-arabinofuranosyl)-5-methyluridine]:

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine:

2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2C_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_{41}$ filtered and evaporated. 275 g of residue was obtained. The residue was purified on a 3.5 kg silica gel column, packed and eluted with EtOAc/-Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-51-O-dimethoxytrityl-5-methyluridine:

2'-O-Methoxyethyl-51-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-51-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methyl-cytidine:

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite:

N$^4$-Benzoyl-2'-O-methoxyethyl-5'-O-dimethoxytrityl-5-methylcytidine (74 g, 0.10 M) was dissolved in CH$_2$Cl$_2$ (1 L) Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tic showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al., Nucl. Acids Res. 1993, 21, 3197–3203) using commercially available phosphoramidites (Glen Research, Sterling Va. or ChemGenes, Needham Mass.).

2'-O-(dimethylaminooxyethyl) nucleoside amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetatehexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethylazodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butylidiphenylsilyl-5-methyluridine as white foam (21.819, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at –10° C. to 0° C. After 1 hr the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eg.) was added and the mixture for 1 hr. Solvent was removed under vacuum; residue chromatographed to get 5'-O-tert-butyldiphenylsilyl-2'-O-[(2-formadoximinooxy) ethyl]-5-methyluridine as white foam (1.95, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

Oligonucleotides having methylene (methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages are synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. (*Acc. Chem. Res.* 1995, 28, 366–374). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al. (*Science* 1991, 254, 1497–1500).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels or capillary gel electrophoresis and judged to be at least 85% full length material. The relative amounts of phosphorothioate and phosphodiester linkages obtained in synthesis were periodically checked by $^{31}$p nuclear magnetic resonance spectroscopy, and for some studies oligonucleotides were purified by HPLC, as described by Chiang et al. (*J. Biol. Chem.* 1991, 266, 18162). Results obtained with HPLC-purified material were similar to those obtained with non-HPLC purified material.

Alternatively, oligonucleotides are synthesized in 96 well plate format via solid phase P(III) phosphoramidite chemistry on an automated synthesizer capable of assembling 96 sequences simultaneously in a standard 96 well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-di-isopropyl phosphoramidites are purchased from commercial vendors (e.g. PE-Applied Biosystems, Foster City, Calif., or Pharmacia, Piscataway, N.J.). Non-standard nucleosides are synthesized as per published methods. They are utilized as base protected beta-cyanoethyldiisopropyl phosphoramidites.

Oligonucleotides were cleaved from support and deprotected with concentrated NH$_4$OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 2
Human FAK Oligonucleotide Sequences

Antisense oligonucleotides were designed to target human FAK. Target sequence data are from the focal adhesion kinase (FAK) cDNA sequence published by Whitney, G. S., et al. (*DNA Cell Biol.*, 1993, 12, 823–830); Genbank accession number L13616, provided herein as SEQ ID NO: 1. One set of oligonucleotides were synthesized as chimeric oligonucleotides ("gapmers"), 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines were 5-methyl-cytosines. These oligonucleotide sequences are shown in Table 1. An identical set of sequences were prepared as fully phosphorothioated oligodeoxynucleotides. These are shown in Table 2. An additional set of oligonucleotides were synthesized as chimeric oligonucleotides ("gapmers"), 15 nucleotides in length, composed of a central "gap" region consisting of five 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines were 5-methyl-cytosines. These oligonucleotide sequences are shown in Table 3. An identical set of sequences were prepared as fully phosphorothioated oligodeoxynucleotides. These are shown in Table 4.

Human A549 lung carcinoma cells (American Type Culture Collection, Manassas, Va.) were grown in DMEM supplemented with 10% fetal bovine serum (FBS), non-essential amino acids for MEM, sodium pyruvate (1 mM), penicillin (50 U/ml) and streptomycin (50 µg/ml). All cell culture reagents were obtained from Life Technologies (Rockville, Md.).

The cells were washed once with OPTIMEMD (Life Technologies, Rockville, Md.), then transfected with 400 nM oligonucleotide and 12 mg/ml LIPOFECTINO (Life Technologies, Rockville, Md.), a 1:1 (w/w) liposome formulation of the cationic lipid N-[1-(2,3-dioleyloxy)propyl]-n,n,n-trimethylammonium chloride (DOTMA), and dioleoyl phosphotidylethanolamine (DOPE) in membrane filtered water. The cells were incubated with oligonucleotide for four hours, after which the media was replaced with fresh media and the cells incubated for another 20 hours.

Total cellular RNA was isolated using an ATLASTM Pure RNA isolation kit (Clontech, Palo Alto, Calif.). RNA was then separated on a 1.2% agarose-formaldehyde gel, transferred to Hybond-N+ membrane (Amersham Pharmacia Biotech, Arlington Heights, Ill.), a positively charged nylon membrane. Immobilized RNA was cross-linked by exposure to UV light. Membranes were probed with either FAK or glyceraldehyde 3-phosphate dehydrogenase (G3PDH) probes. The probes were labeled by random primer using the PRIME-A-GENE® Labeling System, Promega, Madison, Wis.) and hybridized to the membranes. mRNA signals were quantitated by a PhosphoImager (Molecular Dynamics, Sunnyvale, Calif.).

Results of an initial screen of the FAK antisense oligonucleotides are shown in Tables 5 (20 mers) and 6 (15 mers). Oligonucleotides 15392 (SEQ ID NO. 3), 15394 (SEQ ID NO. 4), 15397 (SEQ ID NO. 6), 15399 (SEQ ID NO. 7), 15401 (SEQ ID NO. 8), 15403 (SEQ ID NO. 9), 15405 (SEQ ID NO. 10), 15407 (SEQ ID NO. 11), 15409 (SEQ ID NO. 12), 15413 (SEQ ID NO. 14), 15415 (SEQ ID NO. 15), 15458 (SEQ ID NO. 16), 15460 (SEQ ID NO. 17), 15421 (SEQ ID NO. 18), 15425 (SEQ ID NO. 20), 15393 (SEQ ID NO. 23), 15406 (SEQ ID NO. 30), 15408 (SEQ ID NO. 31) and 15412 (SEQ ID NO. 33) resulted in about 50% or greater inhibition of FAK mRNA expression in this assay. Oligonucleotides 15401 (SEQ ID NO. 8), 15403 (SEQ ID NO. 9), 15409 (SEQ ID NO. 12), 15413 (SEQ ID NO. 14), 15415 (SEQ ID NO. 15), and 15421 (SEQ ID NO. 18) resulted in about 80% or greater inhibition of FAK mRNA expression.

TABLE 1

Nucleotide Sequences of Human FAK Chimeric (deoxy gapped) 20 mer Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 15392 | CCGCGGGCTCACAGTGGTCG | 3 | 0001–0020 | 5'-UTR |
| 15394 | GGCGCCGTGAAGCGAAGGCA | 4 | 0078–0097 | 5'-UTR |
| 15395 | CAGTTCTGCTCGGACCGCGG | 5 | 0101–0120 | 5'-UTR |
| 15397 | GAAACTGCAGAAGGCACTGA | 6 | 0150–0169 | 5'-UTR |
| 15399 | TTCTCCCTTCCGTTATTCTT | 7 | 0183–0202 | 5'-UTR |
| 15401 | CTAGATGCTAGGTATCTGTC | 8 | 0206–0225 | 5'-UTR |
| 15403 | TTTTGCTAGATGCTAGGTAT | 9 | 0211–0230 | 5'-UTR |
| 15405 | GGTAAGCAGCTGCCATTATT | 10 | 0229–0248 | start |
| 15407 | AGTACCCAGGTGAGTCTTAG | 11 | 0285–0304 | coding |
| 15409 | CCTGACATCAGTAGCATCTC | 12 | 0408–0427 | coding |
| 15411 | GTTGGCTTATCTTCAGTAAA | 13 | 0641–0660 | coding |
| 15413 | GGTTAGGGATGGTGCCGTCA | 14 | 1218–1237 | coding |
| 15415 | TGTTGGTTTCCAATCGGACC | 15 | 2789–2808 | coding |
| 15417 | CTAGGGGAGGCTCAGTGTGG | 16 | 3383–3402 | stop |
| 15419 | ATTCCTCGCTGCTGGTGGAA | 17 | 3444–3463 | 3'-UTR |
| 15421 | TTTCAACCAGATGGTCATTC | 18 | 3510–3529 | 3'-UTR |
| 15423 | TTCTGAATATCATGATTGAA | 19 | 3590–3609 | 3'-UTR |
| 15425 | CATGATGCTTAAAAGCTTAC | 20 | 3658–3677 | 3'-UTR |
| 15427 | AATGTGAACATAAATTGTTC | 21 | 3680–3699 | 3'-UTR |
| 15429 | AAGGTAGTTTAGGAATTAAG | 22 | 3738–3757 | 3'-UTR |

[1]Emboldened residues are 2'-methoxyethoxy residues, 2'-methoxyethoxy cytosine residues are 5-methyl-cytosines; all linkages are phosphorothioate linkages.
[2]Coordinates from Genbank Accession No. L13616, locus name "HUMFAKX", SEQ ID NO. 1.

TABLE 2

Nucleotide Sequences of Human FAK 20 mer Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 15432 | CCGCGGGCTCACAGTGGTCG | 3 | 0001–0020 | 5'-UTR |
| 15434 | GGCGCCGTGAAGCGAAGGCA | 4 | 0078–0097 | 5'-UTR |
| 15436 | CAGTTCTGCTCGGACCGCGG | 5 | 0101–0120 | 5'-UTR |
| 15438 | GAAACTGCAGAAGGCACTGA | 6 | 0150–0169 | 5'-UTR |
| 15440 | TTCTCCCTTCCGTTATTCTT | 7 | 0183–0202 | 5'-UTR |
| 15442 | CTAGATGCTAGGTATCTGTC | 8 | 0206–0225 | 5'-UTR |
| 15444 | TTTTGCTAGATGCTAGGTAT | 9 | 0211–0230 | 5'-UTR |
| 15446 | GGTAAGCAGCTGCCATTATT | 10 | 0229–0248 | start |
| 15448 | AGTACCCAGGTGAGTCTTAG | 11 | 0285–0304 | coding |
| 15450 | CCTGACATCAGTAGCATCTC | 12 | 0408–0427 | coding |
| 15452 | GTTGGCTTATCTTCAGTAAA | 13 | 0641–0660 | coding |
| 15454 | GGTTAGGGATGGTGCCGTCA | 14 | 1218–1237 | coding |
| 15456 | TGTTGGTTTCCAATCGGACC | 15 | 2789–2808 | coding |
| 15458 | CTAGGGGAGGCTCAGTGTGG | 16 | 3383–3402 | stop |
| 15460 | ATTCCTCGCTGCTGGTGGAA | 17 | 3444–3463 | 3'-UTR |
| 15462 | TTTCAACCAGATGGTCATTC | 18 | 3510–3529 | 3'-UTR |
| 15464 | TTCTGAATATCATGATTGAA | 19 | 3590–3609 | 3'-UTR |
| 15466 | CATGATGCTTAAAAGCTTAC | 20 | 3658–3677 | 3'-UTR |
| 15468 | AATGTGAACATAAATTGTTC | 21 | 3680–3699 | 3'-UTR |
| 15470 | AAGGTAGTTTAGGAATTAAG | 22 | 3738–3757 | 3'-UTR |

[1]All linkages are phosphorothioate linkages.
[2]Coordinates from Genbank Accession No. L13616, locus name "HUMFAKX", SEQ ID NO. 1.

TABLE 3

Nucleotide Sequences of Human FAK Chimeric (deoxy gapped) 15 mer Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 15393 | GCGGGCTCACAGTGG | 23 | 0004–0018 | 5'-UTR |
| 15431 | CGCCGTGAAGCGAAG | 24 | 0081–0095 | 5'-UTR |
| 15396 | GTTCTGCTCGGACCG | 25 | 0104–0118 | 5'-UTR |
| 15398 | AACTGCAGAAGGCAC | 26 | 0153–0167 | 5'-UTR |
| 15400 | CTCCCTTCCGTTATT | 27 | 0186–0200 | 5'-UTR |
| 15402 | AGATGCTAGGTATCT | 28 | 0209–0223 | 5'-UTR |
| 15404 | TTGCTAGATGCTAGG | 29 | 0214–0228 | 5'-UTR |
| 15406 | TAAGCAGCTGCCATT | 30 | 0232–0246 | start |
| 15408 | TACCCAGGTGAGTCT | 31 | 0288–0302 | coding |
| 15410 | TGACATCAGTAGCAT | 32 | 0411–0425 | coding |
| 15412 | TGGCTTATCTTCAGT | 33 | 0644–0658 | coding |
| 15414 | TTAGGGATGGTGCCG | 34 | 1221–1235 | coding |
| 15416 | TTGGTTTCCAATCGG | 35 | 2792–2806 | coding |
| 15418 | AGGGGAGGCTCAGTG | 36 | 3386–3400 | stop |
| 15420 | TCCTCGCTGCTGGTG | 37 | 3447–3461 | 3'-UTR |
| 15422 | TCAACCAGATGGTCA | 38 | 3513–3527 | 3'-UTR |
| 15424 | CTGAATATCATGATT | 39 | 3593–3607 | 3'-UTR |
| 15426 | TGATGCTTAAAAGCT | 40 | 3661–3675 | 3'-UTR |
| 15428 | TGTGAACATAAATTG | 41 | 3683–3697 | 3'-UTR |
| 15430 | GGTAGTTTAGGAATT | 42 | 3741–3755 | 3'-UTR |

[1]Emboldened residues are 2'-methoxyethoxy residues, 2'-methoxyethoxy cytosine residues are 5-methyl-cytosines; all linkages are phosphorothioate linkages.
[2]Coordinates from Genbank Accession No. L13616, locus name "HUMFAKX", SEQ ID NO. 1.

TABLE 4

Nucleotide Sequences of Human FAK 15 mer Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 15433 | GCGGGCTCACAGTGG | 23 | 0004–0018 | 5'-UTR |
| 15435 | CGCCGTGAAGCGAAG | 24 | 0081–0095 | 5'-UTR |
| 15437 | GTTCTGCTCGGACCG | 25 | 0104–0118 | 5'-UTR |
| 15439 | AACTGCAGAAGGCAC | 26 | 0153–0167 | 5'-UTR |
| 15441 | CTCCCTTCCGTTATT | 27 | 0186–0200 | 5'-UTR |
| 15443 | AGATGCTAGGTATCT | 28 | 0209–0223 | 5'-UTR |
| 15445 | TTGCTAGATGCTAGG | 29 | 0214–0228 | 5'-UTR |
| 15447 | TAAGCAGCTGCCATT | 30 | 0232–0246 | start |
| 15449 | TACCCAGGTGAGTCT | 31 | 0288–0302 | coding |
| 15451 | TGACATCAGTAGCAT | 32 | 0411–0425 | coding |
| 15453 | TGGCTTATCTTCAGT | 33 | 0644–0658 | coding |
| 15455 | TTAGGGATGGTGCCG | 34 | 1221–1235 | coding |
| 15457 | TTGGTTTCCAATCGG | 35 | 2792–2806 | coding |
| 15459 | AGGGGAGGCTCAGTG | 36 | 3386–3400 | stop |
| 15461 | TCCTCGCTGCTGGTG | 37 | 3447–3461 | 3'-UTR |
| 15463 | TCAACCAGATGGTCA | 38 | 3513–3527 | 3'-UTR |
| 15465 | CTGAATATCATGATT | 39 | 3593–3607 | 3'-UTR |
| 15467 | TGATGCTTAAAAGCT | 40 | 3661–3675 | 3'-UTR |
| 15469 | TGTGAACATAAATTG | 41 | 3683–3697 | 3'-UTR |
| 15471 | GGTAGTTTAGGAATT | 42 | 3741–3755 | 3'-UTR |

[1]All linkages are phosphorothioate linkages.
[2]Coordinates from Genbank Accession No. L13616, locus name "HUMFAKX", SEQ ID NO. 1.

TABLE 5

Inhibition of Human Fak mRNA expression in A549 Cells by FAK 20 mer Antisense Oligonucleotides

| ISIS No: | SEQ ID NO: | GENE TARGET REGION | % mRNA EXPRESSION | % mRNA INHIBITION |
|---|---|---|---|---|
| control | — | — | 100% | 0% |
| 15392 | 3 | 5'-UTR | 29% | 71% |
| 15432 | 3 | 5'-UTR | 108% | — |
| 15394 | 4 | 5'-UTR | 30% | 70% |
| 15434 | 4 | 5'-UTR | 147% | — |
| 15395 | 5 | 5'-UTR | 57% | 43% |
| 15436 | 5 | 5'-UTR | 88% | 12% |
| 15397 | 6 | 5'-UTR | 31% | 69% |
| 15438 | 6 | 5'-UTR | 64% | 36% |
| 15399 | 7 | 5'-UTR | 48% | 52% |
| 15440 | 7 | 5'-UTR | 92% | 8% |
| 15401 | 8 | 5'-UTR | 17% | 83% |
| 15442 | 8 | 5'-UTR | 63% | 37% |
| 15403 | 9 | 5'-UTR | 17% | 83% |
| 15444 | 9 | 5'-UTR | 111% | — |
| 15405 | 10 | start | 46% | 54% |
| 15446 | 10 | start | 145% | — |
| 15407 | 11 | coding | 36% | 64% |
| 15448 | 11 | coding | 90% | 10% |
| 15409 | 12 | coding | 13% | 87% |
| 15450 | 12 | coding | 149% | — |
| 15411 | 13 | coding | 70% | 30% |
| 15452 | 13 | coding | 129% | — |
| 15413 | 14 | coding | 22% | 78% |
| 15454 | 14 | coding | 82% | 18% |
| 15415 | 15 | coding | 20% | 80% |
| 15456 | 15 | coding | 88% | 12% |
| 15417 | 16 | stop | 56% | 44% |
| 15458 | 16 | stop | 39% | 61% |
| 15419 | 17 | 3'-UTR | 55% | 45% |
| 15460 | 17 | 3'-UTR | 42% | 58% |
| 15421 | 18 | 3'-UTR | 20% | 80% |
| 15462 | 18 | 3'-UTR | 60% | 40% |
| 15423 | 19 | 3'-UTR | 55% | 45% |
| 15464 | 19 | 3'-UTR | 97% | 3% |
| 15425 | 20 | 3'-UTR | 51% | 49% |
| 15466 | 20 | 3'-UTR | 74% | 26% |
| 15427 | 21 | 3'-UTR | 67% | 33% |
| 15468 | 21 | 3'-UTR | 131% | — |
| 15429 | 22 | 3'-UTR | 57% | 43% |
| 15470 | 22 | 3'-UTR | 71% | 29% |

TABLE 6

Inhibition of Human Fak mRNA expression in A549 Cells by FAK 15 mer antisense oligonucleotides

| ISIS No: | SEQ ID NO: | GENE TARGET REGION | % mRNA EXPRESSION | % mRNA INHIBITION |
|---|---|---|---|---|
| control | — | — | 100% | 0% |
| 15393 | 23 | 5'-UTR | 40% | 60% |
| 15433 | 23 | 5'-UTR | 160% | — |
| 15431 | 24 | 5'-UTR | 59% | 41% |
| 15435 | 24 | 5'-UTR | 121% | — |
| 15396 | 25 | 5'-UTR | 76% | 24% |
| 15437 | 25 | 5'-UTR | 123% | — |
| 15398 | 26 | 5'-UTR | 72% | 28% |
| 15439 | 26 | 5'-UTR | 64% | 36% |
| 15400 | 27 | 5'-UTR | 79% | 21% |
| 15441 | 27 | 5'-UTR | 66% | 34% |
| 15402 | 28 | 5'-UTR | 69% | 31% |
| 15443 | 28 | 5'-UTR | 99% | 1% |
| 15404 | 29 | 5'-UTR | 70% | 30% |
| 15445 | 29 | 5'-UTR | 151% | — |
| 15406 | 30 | start | 32% | 68% |
| 15447 | 30 | start | 69% | 31% |
| 15408 | 31 | coding | 35% | 65% |
| 15449 | 31 | coding | 89% | 11% |
| 15410 | 32 | coding | 67% | 33% |
| 15451 | 32 | coding | 142% | — |
| 15412 | 33 | coding | 43% | 57% |
| 15453 | 33 | coding | 115% | — |
| 15414 | 34 | coding | 64% | 36% |
| 15455 | 34 | coding | 59% | 41% |
| 15416 | 35 | coding | 69% | 31% |
| 15457 | 35 | coding | 121% | — |
| 15418 | 36 | stop | 140% | — |
| 15459 | 36 | stop | 72% | 28% |
| 15420 | 37 | 3'-UTR | 158% | — |
| 15461 | 37 | 3'-UTR | 62% | 38% |
| 15422 | 38 | 3'-UTR | 153% | — |
| 15463 | 38 | 3'-UTR | 91% | 9% |
| 15424 | 39 | 3'-UTR | 207% | — |
| 15465 | 39 | 3'-UTR | 88% | 12% |
| 15426 | 40 | 3'-UTR | 171% | — |
| 15467 | 40 | 3'-UTR | 105% | — |
| 15428 | 41 | 3'-UTR | 95% | 5% |
| 15469 | 41 | 3'-UTR | 96% | 4% |
| 15430 | 42 | 3'-UTR | 137% | — |
| 15471 | 42 | 3'-UTR | 131% | — |

Example 3

Dose response of antisense phosphorothioate oligonucleotide effects on FAK levels in A549 cells Several of the more active oligonucleotides were chosen for a dose response study. A549 cells were grown, treated and processed as described in Example 2, except the concentration of oligonucleotide was varied.

Results are shown in Table 7. Many oligonucleotides showed $IC_{50}$s of 50 nM or less and maximal inhibition seen was 95%.

TABLE 7

Dose Response of A549 cells to FAK Phosphorothioate Oligonucleotides

| ISIS # | SEQ ID NO: | ASO Gene Target | Dose | % mRNA Expression | % mRNA Inhibition |
|---|---|---|---|---|---|
| control | — | — | — | 100.0% | — |
| 15932 | 3 | 5'-UTR | 50 nM | 80.3% | 19.7% |
| " | " | " | 200 nM | 41.6% | 58.4% |
| " | " | " | 400 nM | 28.3% | 71.7% |
| 15393 | 23 | 5'-UTR | 50 nM | 116.6% | — |
| " | " | " | 200 nM | 87.8% | 12.2% |
| " | " | " | 400 nM | 60.7% | 39.3% |
| 15401 | 8 | 5'-UTR | 50 nM | 31.9% | 68.1% |
| " | " | " | 200 nM | 26.8% | 73.2% |
| " | " | " | 400 nM | 20.4% | 79.6% |
| 15403 | 9 | 5'-UTR | 50 nM | 82.7% | 17.3% |
| " | " | " | 200 nM | 27.8% | 72.2% |
| " | " | " | 400 nM | 18.6% | 81.4% |
| 15406 | 30 | start | 50 nM | 51.6% | 48.4% |
| " | " | " | 200 nM | 40.5% | 59.5% |
| " | " | " | 400 nM | 39.3% | 60.7% |
| 15408 | 31 | coding | 50 nM | 47.7% | 52.3% |
| " | " | " | 200 nM | 67.8% | 32.2% |
| " | " | " | 400 nM | 53.2% | 46.8% |
| 15409 | 12 | coding | 50 nM | 30.1% | 69.9% |
| " | " | " | 200 nM | 29.7% | 70.3% |
| " | " | " | 400 nM | 18.9% | 81.1% |
| 15413 | 14 | coding | 50 nM | 45.6% | 54.4% |
| " | " | " | 200 nM | 21.6% | 78.4% |

TABLE 7-continued

Dose Response of A549 cells to FAK
Phosphorothioate Oligonucleotides

| ISIS # | SEQ ID NO: | ASO Gene Target | Dose | % mRNA Expression | % mRNA Inhibition |
|---|---|---|---|---|---|
| " | " | " | 400 nM | 20.6% | 79.4% |
| 15415 | 15 | coding | 50 nM | 46.9% | 53.1% |
| " | " | " | 200 nM | 18.0% | 82.0% |
| " | " | " | 400 nM | 8.0% | 92.0% |
| 15421 | 18 | 3'-UTR | 50 nM | 25.0% | 75.0% |
| " | " | " | 200 nM | 14.8% | 85.2% |
| " | " | " | 400 nM | 5.0% | 95.0% |

A dose response experiment on protein levels was done with two oligonucleotides. A549 cells were grown and treated as described in Example 2 except the concentration was varied as shown in Table 3. The LIPOFECTIN® to oligonucleotide ratio was maintained at 3 mg/ml LIPOFECTIN® per 100 nM oligonucleotide. FAK protein levels were determined 48 hours after antisense treatment in whole cell lysates by anti-FAK blotting. Cells on 10cm plates were lysed with 0.5 ml modified RIPA lysis buffer, diluted with 0.5 ml HNTG buffer (50 mM HEPES, pH 7.4, 150 mM NaCl, 0.1% Triton X-100, 10% glycerol), incubated with agarose beads, and cleared by centrifugation. Immunoprecipitations with a polyclonal FAK antibody (Salk Institute of Biological Studies, La Jolla, Calif.; additional FAK antibodies available from Upstate Biotechnology Incorporated, Lake Placid, N.Y.) were performed for 4hr at 4° C., collected on protein A (Repligen, Cambridge, Mass.) or protein G-plus (Calbiochem) agarose beads, and the precipitated protein complexes were washed at 4° C. in Triton only lysis buffer (modified RIPA without sodium deoxycholate and SDS) followed by washing in HNTG buffer prior to direct analysis by SDS-PAGE. For immunoblotting, proteins were transferred to polyvinylidene fluoride membranes (Millipore) and incubated with a 1:1000 dilution of polyclonal antibody for 2 hr at room temperature. Bound primary antibody was visualized by enhanced chemiluminescent detection.

Results are shown in Table 8.

TABLE 8

Dose Response of A549 cells to FAK
Phosphorothioate Oligonucleotides

| ISIS # | SEQ ID NO: | ASO Gene Target | Dose | % protein Expression | % protein Inhibition |
|---|---|---|---|---|---|
| control | — | — | — | 100% | — |
| 15409 | 12 | coding | 25 nM | 60% | 40% |
| " | " | " | 100 nM | 57% | 43% |
| " | " | " | 200 nM | 23% | 77% |
| 15421 | 18 | 3'-UTR | 25 nM | 73% | 27% |
| " | " | " | 100 nM | 34% | 66% |
| " | " | " | 200 nM | 24% | 76% |

Example 4
Effect of FAK antisense phosphorothioate oligonucleotides on growth factor stimulated migration and invasion Integrin-regulated focal adhesion kinase (FAK) is an important component of epidermal (EGF) and platelet-drived (PDGF) growth factor-induced motility of primary fibroblasts, smooth muscle, and adenocarcinoma cells. To measure the effect of FAK antisense oligonucleotides on cell migration, a modified Boyden chamber (Millipore, Bedford, Mass.) assay was used (Sieg, D. J., et al., *J. Cell Sci.*, 1999, 112, 2677–2691). Both membrane sides were coated with rat tail collagen (5 µg/ml in PBS, Boehringer Mannheim) for 2 hr at 37° C., washed with PBS, and the chambers were placed into 24 well dishes containing migration media (0.5 ml DMEM containing 0.5% BSA) with or without human recombinant PDGF-BB, EGF, or basic-FGF (Calbiochem, San Diego, Calif.) at the indicated concentrations. Serum-starved A549 cells ($1 \times 10^5$ cells in 0.3 ml migration media) were added to the upper chamber and after 3 hr at 37° C., the cells on the membrane upper surface were removed by a cotton tip applicator, the migratory cells on the lower membrane surface were fixed, stained (0.1% crystal violet, 0.1 M borate pH 9.0, 2% EtOH), and the dye eluted for absorbance measurements at 600 nM. Individual experiments represent the average from three individual chambers. Background levels of cell migration (less than 5% of total) in the absence of chemotaxis stimuli (0.5% BSA only) were subtracted from all points.

Results are shown in Table 9. ISIS 17636 (SEQ ID NO. 43) is a five base mismatch control oligonucleotide for ISIS 15421 (SEQ ID NO. 18).

TABLE 9

Effect of FAK Antisense Phosphorothioate Oligonucleotides
on EGF-Stimulated Cell Migration

| ISIS # | SEQ ID NO: | ASO Gene Target | EGF (ng/ml) | $A_{600}$ |
|---|---|---|---|---|
| control | — | — | 2.5 | 0.74 |
| 15421 | 18 | 3'-UTR | " | 0.26 |
| 17636 | 43 | control | " | 0.90 |
| control | — | — | 5.0 | 0.89 |
| 15421 | 18 | 3'-UTR | " | 0.25 |
| 17636 | 43 | control | " | 0.77 |

FAK antisense oligonucleotides were tested in an in vitro invasion assay using an ~1 mm MATRIGELD (Becton Dickinson, Franklin Lakes, N.J.) basement membrane barrier (Albini, A., *Pathol. Oncol. Res.*, 1998, 4, 230–241). Migration chambers were coated with the indicated concentration of MATRIGEL®, dried under laminar flow and then rehydrated with cold serum free DMEM for 90 min on an orbital shaker. A549 cells were grown and transfected as described in Example 2. Cells ($1 \times 10^5$) were then placed onto the MATRIGEL® coated membrane and allowed to invade through the MATRIGEL® towards a 10% FBS chemoattractant for the indicated times. Cells that invaded through the MATRIGEL® were visualized by crystal violet staining as detailed in the migration assay. The amount of MATRIGEL® was varied in the assay to show that invasion was being measured and that the migration was not serum-induced.

Results are shown in Table 10.

TABLE 10

Effect of FAK Antisense Phosphorothioate Oligonucleotides
on Tumor Cell Invasion

| ISIS # | SEQ ID NO: | ASO Gene Target | MATRIGEL ® (µg/chamber) | Migration ($A_{600}$) |
|---|---|---|---|---|
| control | — | — | 0 | 8.3 |
| 15421 | 18 | 3'-UTR | " | 2.8 |
| 17636 | 43 | control | " | 9.9 |
| control | — | — | 15 | 4.5 |
| 15421 | 18 | 3'-UTR | " | 2.0 |

TABLE 10-continued

Effect of FAK Antisense Phosphorothioate Oligonucleotides on Tumor Cell Invasion

| ISIS # | SEQ ID NO: | ASO Gene Target | MATRIGEL ® (µg/chamber) | Migration (A$_{600}$) |
|---|---|---|---|---|
| 17636 | 43 | control | " | 4.3 |
| control | — | — | 26 | 1.6 |
| 15421 | 18 | 3'-UTR | " | 0.7 |
| 17636 | 43 | control | " | 1.3 |

Example 5

FAK antisense oligonucleotides in a retinal neovascularization model

FAK antisense oligonucleotides were tested in a rabbit model of retinal neovascularization (Kimura, H., et al., *Invest. Opthalmol. Vis. Sci.*, 1995, 36, 2110–2119). In this model, growth factors are encapsulated and injected beneath the retina.

Eight male Dutch Belt rabbits and one male Black Satin/New Zealand White Cross rabbit were used in this study. ISIS 15409 (SEQ ID NO. 12) was administered intravitreally by injection, once prior to surgical implantation of the polymeric pellets and once during pellet implantation. Retinal neovascularization was monitored by indirect opthalmolscopy and documented by fundus photography. Retinal neovascularization was graded on a scale from 1 to 5, with one being normal and five showing retinal hemorrhaging and/or detachment. In animals injected with saline and the growth factor containing pellets, evidence of retinal neovascularization could be detected in the first week and retinal hemorrhaging began by the end of the third week. Animals receiving the antisense FAK oligonucleotide showed no evidence of retinal neovascularization over a four week period.

What is claimed is:

1. An antisense compound 8 to 30 nucleobases in length targeted to nucleobases 1–120 of the 5'-untranslated region, nucleobases 150–230 of the 5'-untranslated region, translational termination region or nucleobases 3424–3679 of the 3'-untranslated region of a nucleic acid molecule encoding human focal adhesion kinase (SEO ID NO: 1), wherein said antisense compound inhibits the expression of said focal adhesion kinase.

2. The antisense compound of claim 1 which is an antisense oligonucleotide.

3. The antisense compound of claim 2 wherein the antisense oligonucleotide has a sequence comprising SEQ ID NO: 3, 4, 6, 7, 8, 9, 16, 17, 18, 20 or 23.

4. The antisense compound of claim 2 wherein the antisense oligonucleotide comprises at least one modified internucleoside linkage.

5. The antisense compound of claim 4 wherein the modified internucleoside linkage is a phosphorothioate linkage.

6. The antisense compound of claim 2 wherein the antisense oligonucleotide comprises at least one modified sugar moiety.

7. The antisense compound of claim 6 wherein the modified sugar moiety is a 2'-O-methoxyethyl moiety.

8. The antisense compound of claim 2 wherein the antisense oligonucleotide comprises at least one modified nucleobase.

9. The antisense compound of claim 8 wherein the modified nucleobase is a 5-methyl cytosine.

10. The antisense compound of claim 2 wherein the antisense oligonucleotide is a chimeric oligonucleotide.

11. A composition comprising the antisense compound of claim 1 and a pharmaceutically acceptable carrier or diluent.

12. The composition of claim 11 further comprising a colloidal dispersion system.

13. The composition of claim 11 wherein the antisense compound is an antisense oligonucleotide.

14. A method of inhibiting the expression of human focal adhesion kinase in cells or tissues comprising contacting said cells or tissues with the antisense in vitro compound of claim 1 so that expression of focal adhesion kinase is inhibited.

15. An antisense compound up to 30 nucleobases in length targeted to the coding region of a nucleic acid molecule encoding human focal adhesion kinase, wherein said antisense compound inhibits the expression of said focal adhesion kinase and has a sequence comprising at least an 8 nucleobasic portion of SEQ ID NO: 11, 12, 14, 15, 30, 31 or 33.

16. The antisense compound of claim 15 which is an antisense oligonucleotide.

17. The antisense compound of claim 16 wherein the antisense oligonucleotide comprises at least one modified internucleoside linkage.

18. The antisense compound of claim 17 wherein the modified internucleoside linkage is a phosphorothioate linkage.

19. The antisense compound of claim 16 wherein the antisense oligonucleotide comprises at least one modified sugar moiety.

20. The antisense compound of claim 19 wherein the modified sugar moiety is a 2'-O-methoxyethyl moiety.

21. The antisense compound of claim 16 wherein the antisense oligonucleotide comprises at least one modified nucleobase.

22. The antisense compound of claim 21 wherein the modified nucleobase is a 5-methyl cytosine.

23. The antisense compound of claim 16 wherein the antisense oligonucleotide is a chimeric oligonucleotide.

24. A composition comprising the antisense compound of claim 15 and a pharmaceutically acceptable carrier or diluent.

25. The composition of claim 24 further comprising a colloidal dispersion system.

26. The composition of claim 24 wherein the antisense compound is an antisense oligonucleotide.

27. A method of inhibiting the expression of human focal adhesion kinase in cells or tissues comprising contacting said cells or tissues in vitro with the antisense compound of claim 15 so that expression of focal adhesion kinase is inhibited.

28. A method of inhibiting neovascularization in the eye associated with expression of focal adhesion kinase in an animal comprising intravitreally administering to said animal a therapeutically or prophylactically effective amount of the antisense compound of claim 3 or 15 targeted to a nucleic acid molecule encoding human focal adhesion kinase wherein said antisense compound inhibits the expression of human focal adhesion kinase.

29. An in vitro method of inhibiting migration of cells associated with expression of focal adhesion kinase comprising administering to said cells a therapeutically or prophylactically effective amount of an antisense compound 8 to 30 nucleobases in length targeted to a nucleic acid molecule encoding human focal adhesion kinase comprising SEQ ID NO: 18 wherein said antisense compound inhibits the expression of human focal adhesion kinase.

* * * * *

UNITED STATES PATENT AND TRADEMARK OFFICE
CERTIFICATE OF CORRECTION

PATENT NO. : 6,133,031
DATED : October 17, 2000
INVENTOR(S) : Monia et al.

It is certified that error appears in the above-identified patent and that said Letters Patent are hereby corrected as shown below:

At Col. 10, Line 52, please delete "21-alkoxyalkoxy" and insert therefor --2'-alkoxyalkoxy--

At Col. 16, Line 56, please delete "51-O" and insert therefor --5'-O--

At Col. 16, Line 58, please delete "51-O" and insert therefor --5'-O--

At. Col. 16, Line 63, please delete "tic" and insert therfor --tlc--

At. Col. 16, Line 63, please delete "tic" and insert therfor --tlc--

At. Col. 16, Line 65, please delete "tic" and insert therfor --tlc--

At Col. 17, Line 11, please delete "51-O" and insert therefor --5'-O--

At. Col. 17, Line 66, please delete "tic" and insert therfor --tlc--

At. Col. 22, Line 34, please delete "ATLASTM" and insert therfor --ATLAS™--

UNITED STATES PATENT AND TRADEMARK OFFICE
CERTIFICATE OF CORRECTION

PATENT NO. : 6,133,031
DATED : October 17, 2000
INVENTOR(S) : Monia et al.

It is certified that error appears in the above-identified patent and that said Letters Patent is hereby corrected as shown below:

At. Col. 57, Line 15, please delete "SEO" and insert therfor --SEQ--

Signed and Sealed this

Eighth Day of May, 2001

Attest:

NICHOLAS P. GODICI

Attesting Officer

Acting Director of the United States Patent and Trademark Office

SEQUENCE LISTING

```
<160> NUMBER OF SEQ ID NOS: 43

<210> SEQ ID NO 1
<211> LENGTH: 3791
<212> TYPE: DNA
<213> ORGANISM: Homo sapiens
<220> FEATURE:
<221> NAME/KEY: CDS
<222> LOCATION: (233)..(3391)
<300> PUBLICATION INFORMATION:
<303> JOURNAL: DNA
<304> VOLUME: 12
<305> ISSUE: 9
<306> PAGES: 823-830
<307> DATE: 1993-11
<308> DATABASE ACCESSION NUMBER: L13616/Genbank
<309> DATABASE ENTRY DATE: 1995-01-02

<400> SEQUENCE: 1
cgaccactgt gagcccgcgg cgtgaggcgt cgggaggaag cgcggctgct gtcgcccagc      60
gccgccccgt cgtcgtctgc cttcgcttca cggcgccgag ccgcggtccg agcagaactg     120
gggctccctt gcatcttcca gttacaaatt cagtgccttc tgcagtttcc ccagagctcc     180
tcaagaataa cggaagggag aatatgacag atacctagca tctagcaaaa ta atg gca     238
                                                                Met Ala
                                                                 1 gct gct tac ctt gac ccc aac ttg aat cac aca cca aat tcg agt act       286
Ala Ala Tyr Leu Asp Pro Asn Leu Asn His Thr Pro Asn Ser Ser Thr
          5                  10                  15 aag act cac ctg ggt act ggt atg gaa cgt tct cct ggt gca atg gag       334
Lys Thr His Leu Gly Thr Gly Met Glu Arg Ser Pro Gly Ala Met Glu
 20                  25                  30 cga gta tta aag gtc ttt cat tat ttt gaa agc aat agt gag cca acc       382
Arg Val Leu Lys Val Phe His Tyr Phe Glu Ser Asn Ser Glu Pro Thr
 35                  40                  45                  50 acc tgg gcc agt att atc agg cat gga gat gct act gat gtc agg ggc       430
Thr Trp Ala Ser Ile Ile Arg His Gly Asp Ala Thr Asp Val Arg Gly
                 55                  60                  65 atc att cag aag ata gtg gac agt cac aaa gta aag cat gtg gcc tgc       478
Ile Ile Gln Lys Ile Val Asp Ser His Lys Val Lys His Val Ala Cys
             70                  75                  80 tat gga ttc cgc ctc agt cac ctg cgg tca gag gag gtt cac tgg ctt       526
Tyr Gly Phe Arg Leu Ser His Leu Arg Ser Glu Glu Val His Trp Leu
         85                  90                  95
```

-continued

```
cac gtg gat atg ggc gtc tcc agt gtg agg gag aag tat gag ctt gct      574
His Val Asp Met Gly Val Ser Ser Val Arg Glu Lys Tyr Glu Leu Ala
        100                 105                 110 cac cca cca gag gag tgg aaa tat gaa ttg aga att cgt tat ttg cca      622
His Pro Pro Glu Glu Trp Lys Tyr Glu Leu Arg Ile Arg Tyr Leu Pro
115                 120                 125                 130 aaa gga ttt cta aac cag ttt act gaa gat aag cca act ttg aat ttc      670
Lys Gly Phe Leu Asn Gln Phe Thr Glu Asp Lys Pro Thr Leu Asn Phe
                135                 140                 145 ttc tat caa cag gtg aag agc gat tat atg tta gag ata gct gat caa      718
Phe Tyr Gln Gln Val Lys Ser Asp Tyr Met Leu Glu Ile Ala Asp Gln
            150                 155                 160 gtg gac cag gaa att gct ttg aag ttg ggt tgt cta gaa ata cgg cga      766
Val Asp Gln Glu Ile Ala Leu Lys Leu Gly Cys Leu Glu Ile Arg Arg
        165                 170                 175 tca tac tgg gag atg cgg ggc aat gca cta gaa aag aag tct aac tat      814
Ser Tyr Trp Glu Met Arg Gly Asn Ala Leu Glu Lys Lys Ser Asn Tyr
180                 185                 190 gaa gta tta gaa aaa gat gtt ggt tta aag cga ttt ttt cct aag agt      862
Glu Val Leu Glu Lys Asp Val Gly Leu Lys Arg Phe Phe Pro Lys Ser
195                 200                 205                 210 tta ctg gat tct gtc aag gcc aaa aca cta aga aaa ctg atc caa caa      910
Leu Leu Asp Ser Val Lys Ala Lys Thr Leu Arg Lys Leu Ile Gln Gln
                215                 220                 225 aca ttt aga caa ttt gcc aac ctt aat aga gaa gaa agt att ctg aaa      958
Thr Phe Arg Gln Phe Ala Asn Leu Asn Arg Glu Glu Ser Ile Leu Lys
            230                 235                 240 ttc ttt gag atc ctg tct cca gtc tac aga ttt gat aag gaa tgc ttc     1006
Phe Phe Glu Ile Leu Ser Pro Val Tyr Arg Phe Asp Lys Glu Cys Phe
        245                 250                 255 aag tgt gct ctt ggt tca agc tgg att att tca gtg gaa ctg gca atc     1054
Lys Cys Ala Leu Gly Ser Ser Trp Ile Ile Ser Val Glu Leu Ala Ile
260                 265                 270 ggc cca gaa gaa gga atc agt tac cta acg gac aag ggc tgc aat ccc     1102
Gly Pro Glu Glu Gly Ile Ser Tyr Leu Thr Asp Lys Gly Cys Asn Pro
275                 280                 285                 290 aca cat ctt gct gac ttc act caa gtg caa acc att cag tat tca aac     1150
Thr His Leu Ala Asp Phe Thr Gln Val Gln Thr Ile Gln Tyr Ser Asn
                295                 300                 305 agt gaa gac aag gac aga aaa gga atg cta caa cta aaa ata gca ggt     1198
Ser Glu Asp Lys Asp Arg Lys Gly Met Leu Gln Leu Lys Ile Ala Gly
            310                 315                 320 gca ccc gag cct ctg aca gtg acg gca cca tcc cta acc att gcg gag     1246
Ala Pro Glu Pro Leu Thr Val Thr Ala Pro Ser Leu Thr Ile Ala Glu
        325                 330                 335 aat atg gct gac cta ata gat ggg tac tgc cgg ctg gtg aat gga acc     1294
Asn Met Ala Asp Leu Ile Asp Gly Tyr Cys Arg Leu Val Asn Gly Thr
340                 345                 350 tcg cag tca ttt atc atc aga cct cag aaa gaa ggt gaa cgg gct ttg     1342
Ser Gln Ser Phe Ile Ile Arg Pro Gln Lys Glu Gly Glu Arg Ala Leu
355                 360                 365                 370 cca tca ata cca aag ttg gcc aac agc gaa aag caa ggc atg cgg aca     1390
Pro Ser Ile Pro Lys Leu Ala Asn Ser Glu Lys Gln Gly Met Arg Thr
                375                 380                 385 cac gcc gtc tct gtg tca gaa aca gat gat tat gct gag att ata gat     1438
His Ala Val Ser Val Ser Glu Thr Asp Asp Tyr Ala Glu Ile Ile Asp
            390                 395                 400 gaa gaa gat act tac acc atg ccc tca acc agg gat tat gag att caa     1486
Glu Glu Asp Thr Tyr Thr Met Pro Ser Thr Arg Asp Tyr Glu Ile Gln
```

```
                    405                 410                 415
aga gaa aga ata gaa ctt gga cga tgt att gga gaa ggc caa ttt gga    1534
Arg Glu Arg Ile Glu Leu Gly Arg Cys Ile Gly Glu Gly Gln Phe Gly
            420                 425                 430 gat gta cat caa ggc att tat atg agt cca gag aat cca gct ttg gcg    1582
Asp Val His Gln Gly Ile Tyr Met Ser Pro Glu Asn Pro Ala Leu Ala
435                 440                 445                 450 gtt gca att aaa aca tgt aaa aac tgt act tcg gac agc gtg aga gag    1630
Val Ala Ile Lys Thr Cys Lys Asn Cys Thr Ser Asp Ser Val Arg Glu
            455                 460                 465 aaa ttt ctt caa gaa gcc tta aca atg cgt cag ttt gac cat cct cat    1678
Lys Phe Leu Gln Glu Ala Leu Thr Met Arg Gln Phe Asp His Pro His
            470                 475                 480 att gtg aag ctg att gga gtc atc aca gag aat cct gtc tgg ata atc    1726
Ile Val Lys Leu Ile Gly Val Ile Thr Glu Asn Pro Val Trp Ile Ile
            485                 490                 495 atg gag ctg tgc aca ctt gga gag ctg agg tca ttt ttg caa gta agg    1774
Met Glu Leu Cys Thr Leu Gly Glu Leu Arg Ser Phe Leu Gln Val Arg
            500                 505                 510 aaa tac agt ttg gat cta gca tct ttg atc ctg tat gcc tat cag ctt    1822
Lys Tyr Ser Leu Asp Leu Ala Ser Leu Ile Leu Tyr Ala Tyr Gln Leu
515                 520                 525                 530 agt aca gct ctt gca tat cta gag agc aaa aga ttt gta cac agg gac    1870
Ser Thr Ala Leu Ala Tyr Leu Glu Ser Lys Arg Phe Val His Arg Asp
            535                 540                 545 att gct gct cgg aat gtt ctg gtg tcc tca aat gat tgt gta aaa tta    1918
Ile Ala Ala Arg Asn Val Leu Val Ser Ser Asn Asp Cys Val Lys Leu
            550                 555                 560 gga gac ttt gga tta tcc cga tat atg gaa gat agt act tac tac aaa    1966
Gly Asp Phe Gly Leu Ser Arg Tyr Met Glu Asp Ser Thr Tyr Tyr Lys
            565                 570                 575 gct tcc aaa gga aaa ttg cct att aaa tgg atg gct cca gag tca atc    2014
Ala Ser Lys Gly Lys Leu Pro Ile Lys Trp Met Ala Pro Glu Ser Ile
580                 585                 590 aat ttt cga cgt ttt acc tca gct agt gac gta tgg atg ttt ggt gtg    2062
Asn Phe Arg Arg Phe Thr Ser Ala Ser Asp Val Trp Met Phe Gly Val
595                 600                 605                 610 tgt atg tgg gag ata ctg atg cat ggt gtg aag cct ttt caa gga gtg    2110
Cys Met Trp Glu Ile Leu Met His Gly Val Lys Pro Phe Gln Gly Val
            615                 620                 625 aag aac aat gat gta atc ggt cga att gaa aat ggg gaa aga tta cca    2158
Lys Asn Asn Asp Val Ile Gly Arg Ile Glu Asn Gly Glu Arg Leu Pro
            630                 635                 640 atg cct cca aat tgt cct cct acc ctc tac agc ctt atg acg aaa tgc    2206
Met Pro Pro Asn Cys Pro Pro Thr Leu Tyr Ser Leu Met Thr Lys Cys
            645                 650                 655 tgg gcc tat gac ccc agc agg cgg ccc agg ttt act gaa ctt aaa gct    2254
Trp Ala Tyr Asp Pro Ser Arg Arg Pro Arg Phe Thr Glu Leu Lys Ala
            660                 665                 670 cag ctc agc aca atc ctg gag gaa gag aag gct cag caa gaa gag cgc    2302
Gln Leu Ser Thr Ile Leu Glu Glu Glu Lys Ala Gln Gln Glu Glu Arg
675                 680                 685                 690 atg agg atg gag tcc aga aga cag gcc aca gtg tcc tgg gac tcc gga    2350
Met Arg Met Glu Ser Arg Arg Gln Ala Thr Val Ser Trp Asp Ser Gly
            695                 700                 705 ggg tct gat gaa gca ccg ccc aag ccc agc aga ccg ggt tat ccc agt    2398
Gly Ser Asp Glu Ala Pro Pro Lys Pro Ser Arg Pro Gly Tyr Pro Ser
            710                 715                 720 ccg agg tcc agc gaa gga ttt tat ccc agc cca cag cac atg gta caa    2446
```

-continued

| | | |
|---|---|---|
| Pro Arg Ser Ser Glu Gly Phe Tyr Pro Ser Pro Gln His Met Val Gln<br>725                    730               735 | | |
| acc aat cat tac cag gtt tct ggc tac cct ggt tca cat gga atc aca<br>Thr Asn His Tyr Gln Val Ser Gly Tyr Pro Gly Ser His Gly Ile Thr<br>740                    745               750 | 2494 | |
| gcc atg gct ggc agc atc tat cca ggt cag gca tct ctt ttg gac caa<br>Ala Met Ala Gly Ser Ile Tyr Pro Gly Gln Ala Ser Leu Leu Asp Gln<br>755                   760               765               770 | 2542 | |
| aca gat tca tgg aat cat aga cct cag gag ata gca atg tgg cag ccc<br>Thr Asp Ser Trp Asn His Arg Pro Gln Glu Ile Ala Met Trp Gln Pro<br>                775               780               785 | 2590 | |
| aat gtg gag gac tct aca gta ttg gac ctg cga ggg att ggg caa gtg<br>Asn Val Glu Asp Ser Thr Val Leu Asp Leu Arg Gly Ile Gly Gln Val<br>          790               795               800 | 2638 | |
| ttg cca acc cat ctg atg gaa gag cgt cta atc cga cag caa cag gaa<br>Leu Pro Thr His Leu Met Glu Glu Arg Leu Ile Arg Gln Gln Gln Glu<br>          805               810               815 | 2686 | |
| atg gaa gaa gat cag cgc tgg ctg gaa aaa gag gaa aga ttt ctg aaa<br>Met Glu Glu Asp Gln Arg Trp Leu Glu Lys Glu Glu Arg Phe Leu Lys<br>820                   825               830 | 2734 | |
| cct gat gtg aga ctc tct cga ggc agt att gac agg gag gat gga agt<br>Pro Asp Val Arg Leu Ser Arg Gly Ser Ile Asp Arg Glu Asp Gly Ser<br>835                   840               845               850 | 2782 | |
| ctt cag ggt ccg att gga aac caa cat ata tat cag cct gtg ggt aaa<br>Leu Gln Gly Pro Ile Gly Asn Gln His Ile Tyr Gln Pro Val Gly Lys<br>                855               860               865 | 2830 | |
| cca gat cct gca gct cca cca aag aaa ccg cct cgc cct gga gct ccc<br>Pro Asp Pro Ala Ala Pro Pro Lys Lys Pro Pro Arg Pro Gly Ala Pro<br>          870               875               880 | 2878 | |
| ggt cat ctg gga agc ctt gcc agc ctc agc agc cct gct gac agc tac<br>Gly His Leu Gly Ser Leu Ala Ser Leu Ser Ser Pro Ala Asp Ser Tyr<br>          885               890               895 | 2926 | |
| aac gag ggt gtc aag ctt cag ccc cag gaa atc agc ccc cct cct act<br>Asn Glu Gly Val Lys Leu Gln Pro Gln Glu Ile Ser Pro Pro Pro Thr<br>900                   905               910 | 2974 | |
| gcc aac ctg gac cgg tcg aat gat aag gtg tac gag aat gtg acg ggc<br>Ala Asn Leu Asp Arg Ser Asn Asp Lys Val Tyr Glu Asn Val Thr Gly<br>915                   920               925               930 | 3022 | |
| ctg gtg aaa gct gtc atc gag atg tcc agt aaa atc cag cca gcc cca<br>Leu Val Lys Ala Val Ile Glu Met Ser Ser Lys Ile Gln Pro Ala Pro<br>                935               940               945 | 3070 | |
| cca gag gag tat gtc cct atg gtg aag gaa gtc ggc ttg gcc ctg agg<br>Pro Glu Glu Tyr Val Pro Met Val Lys Glu Val Gly Leu Ala Leu Arg<br>          950               955               960 | 3118 | |
| aca tta ttg gcc act gtg gat gag acc att ccc ctc cta cca gcc agc<br>Thr Leu Leu Ala Thr Val Asp Glu Thr Ile Pro Leu Leu Pro Ala Ser<br>          965               970               975 | 3166 | |
| acc cac cga gag att gag atg gca cag aag cta ttg aac tct gac ctg<br>Thr His Arg Glu Ile Glu Met Ala Gln Lys Leu Leu Asn Ser Asp Leu<br>980                   985               990 | 3214 | |
| ggt gag ctc atc aac aag atg aaa ctg gcc cag cag tat gtc atg acc<br>Gly Glu Leu Ile Asn Lys Met Lys Leu Ala Gln Gln Tyr Val Met Thr<br>995                  1000              1005             1010 | 3262 | |
| agc ctc cag caa gag tac aaa aag caa atg ctg act gct gct cac gcc<br>Ser Leu Gln Gln Glu Tyr Lys Lys Gln Met Leu Thr Ala Ala His Ala<br>                1015              1020             1025 | 3310 | |
| ctg gct gtg gat gcc aaa aac tta ctc gat gtc att gac caa gca aga<br>Leu Ala Val Asp Ala Lys Asn Leu Leu Asp Val Ile Asp Gln Ala Arg<br>1030                 1035              1040 | 3358 | |

-continued

```
ctg aaa atg ctt ggg cag acg aga cca cac tga gcctcccta ggagcacgtc    3411
Leu Lys Met Leu Gly Gln Thr Arg Pro His
        1045                1050 ttgctaccct cttttgaaga tgttctctag ccttccacca gcagcgagga attaaccctg    3471
tgtcctcagt cgccagcact tacagctcca acttttttga atgaccatct ggttgaaaaa    3531
tctttctcat ataagtttaa ccacactttg atttgggttc attttttgtt ttgtttttt     3591 caatcatgat attcagaaaa atccaggatc caaaatgtgg cgttttttcta agaatgaaaa    3651 ttatatgtaa gcttttaagc atcatgaaga acaatttatg ttcacattaa gatacgttct    3711 aaaggggat ggccaagggg tgacatctta attcctaaac taccttagct gcatagtgga     3771
agaggagagc tagaagcaaa                                                 3791
```

<210> SEQ ID NO 2
<211> LENGTH: 1052
<212> TYPE: PRT
<213> ORGANISM: Homo sapiens

<400> SEQUENCE: 2

```
Met Ala Ala Tyr Leu Asp Pro Asn Leu Asn His Thr Pro Asn Ser
 1               5                  10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
        35                  40                  45

Pro Thr Thr Trp Ala Ser Ile Ile Arg His Gly Asp Ala Thr Asp Val
    50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
                85                  90                  95

Trp Leu His Val Asp Met Gly Val Ser Ser Val Arg Glu Lys Tyr Glu
            100                 105                 110

Leu Ala His Pro Pro Glu Glu Trp Lys Tyr Glu Leu Arg Ile Arg Tyr
        115                 120                 125

Leu Pro Lys Gly Phe Leu Asn Gln Phe Thr Glu Asp Lys Pro Thr Leu
    130                 135                 140

Asn Phe Phe Tyr Gln Gln Val Lys Ser Asp Tyr Met Leu Glu Ile Ala
145                 150                 155                 160

Asp Gln Val Asp Gln Glu Ile Ala Leu Lys Leu Gly Cys Leu Glu Ile
                165                 170                 175

Arg Arg Ser Tyr Trp Glu Met Arg Gly Asn Ala Leu Glu Lys Lys Ser
            180                 185                 190

Asn Tyr Glu Val Leu Glu Lys Asp Val Gly Leu Lys Arg Phe Phe Pro
        195                 200                 205

Lys Ser Leu Leu Asp Ser Val Lys Ala Lys Thr Leu Arg Lys Leu Ile
    210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
            260                 265                 270

Ala Ile Gly Pro Glu Glu Gly Ile Ser Tyr Leu Thr Asp Lys Gly Cys
        275                 280                 285
```

```
Asn Pro Thr His Leu Ala Asp Phe Thr Gln Val Gln Thr Ile Gln Tyr
    290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
                325                 330                 335

Ala Glu Asn Met Ala Asp Leu Ile Asp Gly Tyr Cys Arg Leu Val Asn
            340                 345                 350

Gly Thr Ser Gln Ser Phe Ile Ile Arg Pro Gln Lys Glu Gly Glu Arg
        355                 360                 365

Ala Leu Pro Ser Ile Pro Lys Leu Ala Asn Ser Glu Lys Gln Gly Met
370                 375                 380

Arg Thr His Ala Val Ser Val Ser Glu Thr Asp Asp Tyr Ala Glu Ile
385                 390                 395                 400

Ile Asp Glu Glu Asp Thr Tyr Thr Met Pro Ser Thr Arg Asp Tyr Glu
                405                 410                 415

Ile Gln Arg Glu Arg Ile Glu Leu Gly Arg Cys Ile Gly Glu Gly Gln
            420                 425                 430

Phe Gly Asp Val His Gln Gly Ile Tyr Met Ser Pro Glu Asn Pro Ala
        435                 440                 445

Leu Ala Val Ala Ile Lys Thr Cys Lys Asn Cys Thr Ser Asp Ser Val
450                 455                 460

Arg Glu Lys Phe Leu Gln Glu Ala Leu Thr Met Arg Gln Phe Asp His
465                 470                 475                 480

Pro His Ile Val Lys Leu Ile Gly Val Ile Thr Glu Asn Pro Val Trp
                485                 490                 495

Ile Ile Met Glu Leu Cys Thr Leu Gly Glu Leu Arg Ser Phe Leu Gln
            500                 505                 510

Val Arg Lys Tyr Ser Leu Asp Leu Ala Ser Leu Ile Leu Tyr Ala Tyr
        515                 520                 525

Gln Leu Ser Thr Ala Leu Ala Tyr Leu Glu Ser Lys Arg Phe Val His
530                 535                 540

Arg Asp Ile Ala Ala Arg Asn Val Leu Val Ser Ser Asn Asp Cys Val
545                 550                 555                 560

Lys Leu Gly Asp Phe Gly Leu Ser Arg Tyr Met Glu Asp Ser Thr Tyr
                565                 570                 575

Tyr Lys Ala Ser Lys Gly Lys Leu Pro Ile Lys Trp Met Ala Pro Glu
            580                 585                 590

Ser Ile Asn Phe Arg Arg Phe Thr Ser Ala Ser Asp Val Trp Met Phe
        595                 600                 605

Gly Val Cys Met Trp Glu Ile Leu Met His Gly Val Lys Pro Phe Gln
610                 615                 620

Gly Val Lys Asn Asn Asp Val Ile Gly Arg Ile Glu Asn Gly Glu Arg
625                 630                 635                 640

Leu Pro Met Pro Pro Asn Cys Pro Pro Thr Leu Tyr Ser Leu Met Thr
                645                 650                 655

Lys Cys Trp Ala Tyr Asp Pro Ser Arg Arg Pro Arg Phe Thr Glu Leu
            660                 665                 670

Lys Ala Gln Leu Ser Thr Ile Leu Glu Glu Glu Lys Ala Gln Gln Glu
        675                 680                 685

Glu Arg Met Arg Met Glu Ser Arg Arg Gln Ala Thr Val Ser Trp Asp
690                 695                 700
```

Ser Gly Gly Ser Asp Glu Ala Pro Pro Lys Pro Ser Arg Pro Gly Tyr
705                 710                 715                 720

Pro Ser Pro Arg Ser Ser Glu Gly Phe Tyr Pro Ser Pro Gln His Met
            725                 730                 735

Val Gln Thr Asn His Tyr Gln Val Ser Gly Tyr Pro Gly Ser His Gly
            740                 745                 750

Ile Thr Ala Met Ala Gly Ser Ile Tyr Pro Gly Gln Ala Ser Leu Leu
            755                 760                 765

Asp Gln Thr Asp Ser Trp Asn His Arg Pro Gln Glu Ile Ala Met Trp
770                 775                 780

Gln Pro Asn Val Glu Asp Ser Thr Val Leu Asp Leu Arg Gly Ile Gly
785                 790                 795                 800

Gln Val Leu Pro Thr His Leu Met Glu Glu Arg Leu Ile Arg Gln Gln
            805                 810                 815

Gln Glu Met Glu Glu Asp Gln Arg Trp Leu Glu Lys Glu Arg Phe
            820                 825                 830

Leu Lys Pro Asp Val Arg Leu Ser Arg Gly Ser Ile Asp Arg Glu Asp
            835                 840                 845

Gly Ser Leu Gln Gly Pro Ile Gly Asn Gln His Ile Tyr Gln Pro Val
850                 855                 860

Gly Lys Pro Asp Pro Ala Ala Pro Pro Lys Lys Pro Pro Arg Pro Gly
865                 870                 875                 880

Ala Pro Gly His Leu Gly Ser Leu Ala Ser Leu Ser Ser Pro Ala Asp
            885                 890                 895

Ser Tyr Asn Glu Gly Val Lys Leu Gln Pro Gln Glu Ile Ser Pro Pro
            900                 905                 910

Pro Thr Ala Asn Leu Asp Arg Ser Asn Asp Lys Val Tyr Glu Asn Val
            915                 920                 925

Thr Gly Leu Val Lys Ala Val Ile Glu Met Ser Ser Lys Ile Gln Pro
            930                 935                 940

Ala Pro Pro Glu Glu Tyr Val Pro Met Val Lys Glu Val Gly Leu Ala
945                 950                 955                 960

Leu Arg Thr Leu Leu Ala Thr Val Asp Glu Thr Ile Pro Leu Leu Pro
            965                 970                 975

Ala Ser Thr His Arg Glu Ile Glu Met Ala Gln Lys Leu Leu Asn Ser
            980                 985                 990

Asp Leu Gly Glu Leu Ile Asn Lys Met Lys Leu Ala Gln Gln Tyr Val
            995                 1000                1005

Met Thr Ser Leu Gln Gln Glu Tyr Lys Lys Gln Met Leu Thr Ala Ala
    1010                1015                1020

His Ala Leu Ala Val Asp Ala Lys Asn Leu Leu Asp Val Ile Asp Gln
1025                1030                1035                1040

Ala Arg Leu Lys Met Leu Gly Gln Thr Arg Pro His
                1045                1050

<210> SEQ ID NO 3
<211> LENGTH: 20
<212> TYPE: DNA
<213> ORGANISM: Artificial Sequence
<220> FEATURE:
<223> OTHER INFORMATION: antisense sequence

<400> SEQUENCE: 3
ccgcgggctc acagtggtcg                                          20

-continued

<210> SEQ ID NO 4
<211> LENGTH: 20
<212> TYPE: DNA
<213> ORGANISM: Artificial Sequence
<220> FEATURE:
<223> OTHER INFORMATION: antisense sequence

<400> SEQUENCE: 4
ggcgccgtga agcgaaggca                                                    20

<210> SEQ ID NO 5
<211> LENGTH: 20
<212> TYPE: DNA
<213> ORGANISM: Artificial Sequence
<220> FEATURE:
<223> OTHER INFORMATION: antisense sequence

<400> SEQUENCE: 5
cagttctgct cggaccgcgg                                                    20

<210> SEQ ID NO 6
<211> LENGTH: 20
<212> TYPE: DNA
<213> ORGANISM: Artificial Sequence
<220> FEATURE:
<223> OTHER INFORMATION: antisense sequence

<400> SEQUENCE: 6
gaaactgcag aaggcactga                                                    20

<210> SEQ ID NO 7
<211> LENGTH: 20
<212> TYPE: DNA
<213> ORGANISM: Artificial Sequence
<220> FEATURE:
<223> OTHER INFORMATION: antisense sequence

<400> SEQUENCE: 7
ttctcccttc cgttattctt                                                    20

<210> SEQ ID NO 8
<211> LENGTH: 20
<212> TYPE: DNA
<213> ORGANISM: Artificial Sequence
<220> FEATURE:
<223> OTHER INFORMATION: antisense sequence

<400> SEQUENCE: 8
ctagatgcta ggtatctgtc                                                    20

<210> SEQ ID NO 9
<211> LENGTH: 20
<212> TYPE: DNA
<213> ORGANISM: Artificial Sequence
<220> FEATURE:
<223> OTHER INFORMATION: antisense sequence

<400> SEQUENCE: 9
ttttgctaga tgctaggtat                                                    20

<210> SEQ ID NO 10
<211> LENGTH: 20
<212> TYPE: DNA
<213> ORGANISM: Artificial Sequence
<220> FEATURE:
<223> OTHER INFORMATION: antisense sequence -continued

```
<400> SEQUENCE: 10
ggtaagcagc tgccattatt                                                   20

<210> SEQ ID NO 11
<211> LENGTH: 20
<212> TYPE: DNA
<213> ORGANISM: Artificial Sequence
<220> FEATURE:
<223> OTHER INFORMATION: antisense sequence

<400> SEQUENCE: 11
agtacccagg tgagtcttag                                                   20

<210> SEQ ID NO 12
<211> LENGTH: 20
<212> TYPE: DNA
<213> ORGANISM: Artificial Sequence
<220> FEATURE:
<223> OTHER INFORMATION: antisense sequence

<400> SEQUENCE: 12
cctgacatca gtagcatctc                                                   20

<210> SEQ ID NO 13
<211> LENGTH: 20
<212> TYPE: DNA
<213> ORGANISM: Artificial Sequence
<220> FEATURE:
<223> OTHER INFORMATION: antisense sequence

<400> SEQUENCE: 13
gttggcttat cttcagtaaa                                                   20

<210> SEQ ID NO 14
<211> LENGTH: 20
<212> TYPE: DNA
<213> ORGANISM: Artificial Sequence
<220> FEATURE:
<223> OTHER INFORMATION: antisense sequence

<400> SEQUENCE: 14
ggttagggat ggtgccgtca                                                   20

<210> SEQ ID NO 15
<211> LENGTH: 20
<212> TYPE: DNA
<213> ORGANISM: Artificial Sequence
<220> FEATURE:
<223> OTHER INFORMATION: antisense sequence

<400> SEQUENCE: 15
tgttggtttc caatcggacc                                                   20

<210> SEQ ID NO 16
<211> LENGTH: 20
<212> TYPE: DNA
<213> ORGANISM: Artificial Sequence
<220> FEATURE:
<223> OTHER INFORMATION: antisense sequence

<400> SEQUENCE: 16
ctaggggagg ctcagtgtgg                                                   20

<210> SEQ ID NO 17
<211> LENGTH: 20
```

```
<212> TYPE: DNA
<213> ORGANISM: Artificial Sequence
<220> FEATURE:
<223> OTHER INFORMATION: antisense sequence

<400> SEQUENCE: 17
attcctcgct gctggtggaa                                                  20

<210> SEQ ID NO 18
<211> LENGTH: 20
<212> TYPE: DNA
<213> ORGANISM: Artificial Sequence
<220> FEATURE:
<223> OTHER INFORMATION: antisense sequence

<400> SEQUENCE: 18
tttcaaccag atggtcattc                                                  20

<210> SEQ ID NO 19
<211> LENGTH: 20
<212> TYPE: DNA
<213> ORGANISM: Artificial Sequence
<220> FEATURE:
<223> OTHER INFORMATION: antisense sequence

<400> SEQUENCE: 19
ttctgaatat catgattgaa                                                  20

<210> SEQ ID NO 20
<211> LENGTH: 20
<212> TYPE: DNA
<213> ORGANISM: Artificial Sequence
<220> FEATURE:
<223> OTHER INFORMATION: antisense sequence

<400> SEQUENCE: 20
catgatgctt aaaagcttac                                                  20

<210> SEQ ID NO 21
<211> LENGTH: 20
<212> TYPE: DNA
<213> ORGANISM: Artificial Sequence
<220> FEATURE:
<223> OTHER INFORMATION: antisense sequence

<400> SEQUENCE: 21
aatgtgaaca taaattgttc                                                  20

<210> SEQ ID NO 22
<211> LENGTH: 20
<212> TYPE: DNA
<213> ORGANISM: Artificial Sequence
<220> FEATURE:
<223> OTHER INFORMATION: antisense sequence

<400> SEQUENCE: 22
aaggtagttt aggaattaag                                                  20

<210> SEQ ID NO 23
<211> LENGTH: 15
<212> TYPE: DNA
<213> ORGANISM: Artificial Sequence
<220> FEATURE:
<223> OTHER INFORMATION: antisense sequence

<400> SEQUENCE: 23
```

-continued gcgggctcac agtgg                                                    15

<210> SEQ ID NO 24
<211> LENGTH: 15
<212> TYPE: DNA
<213> ORGANISM: Artificial Sequence
<220> FEATURE:
<223> OTHER INFORMATION: antisense sequence

<400> SEQUENCE: 24
cgccgtgaag cgaag                                                    15

<210> SEQ ID NO 25
<211> LENGTH: 15
<212> TYPE: DNA
<213> ORGANISM: Artificial Sequence
<220> FEATURE:
<223> OTHER INFORMATION: antisense sequence

<400> SEQUENCE: 25
gttctgctcg gaccg                                                    15

<210> SEQ ID NO 26
<211> LENGTH: 15
<212> TYPE: DNA
<213> ORGANISM: Artificial Sequence
<220> FEATURE:
<223> OTHER INFORMATION: antisense sequence

<400> SEQUENCE: 26
aactgcagaa ggcac                                                    15

<210> SEQ ID NO 27
<211> LENGTH: 15
<212> TYPE: DNA
<213> ORGANISM: Artificial Sequence
<220> FEATURE:
<223> OTHER INFORMATION: antisense sequence

<400> SEQUENCE: 27
ctcccttccg ttatt                                                    15

<210> SEQ ID NO 28
<211> LENGTH: 15
<212> TYPE: DNA
<213> ORGANISM: Artificial Sequence
<220> FEATURE:
<223> OTHER INFORMATION: antisense sequence

<400> SEQUENCE: 28
agatgctagg tatct                                                    15

<210> SEQ ID NO 29
<211> LENGTH: 15
<212> TYPE: DNA
<213> ORGANISM: Artificial Sequence
<220> FEATURE:
<223> OTHER INFORMATION: antisense sequence

<400> SEQUENCE: 29
ttgctagatg ctagg                                                    15

<210> SEQ ID NO 30
<211> LENGTH: 15
<212> TYPE: DNA
<213> ORGANISM: Artificial Sequence

```
<220> FEATURE:
<223> OTHER INFORMATION: antisense sequence

<400> SEQUENCE: 30
taagcagctg ccatt                                                15

<210> SEQ ID NO 31
<211> LENGTH: 15
<212> TYPE: DNA
<213> ORGANISM: Artificial Sequence
<220> FEATURE:
<223> OTHER INFORMATION: antisense sequence

<400> SEQUENCE: 31
tacccaggtg agtct                                                15

<210> SEQ ID NO 32
<211> LENGTH: 15
<212> TYPE: DNA
<213> ORGANISM: Artificial Sequence
<220> FEATURE:
<223> OTHER INFORMATION: antisense sequence

<400> SEQUENCE: 32
tgacatcagt agcat                                                15

<210> SEQ ID NO 33
<211> LENGTH: 15
<212> TYPE: DNA
<213> ORGANISM: Artificial Sequence
<220> FEATURE:
<223> OTHER INFORMATION: antisense sequence

<400> SEQUENCE: 33
tggcttatct tcagt                                                15

<210> SEQ ID NO 34
<211> LENGTH: 15
<212> TYPE: DNA
<213> ORGANISM: Artificial Sequence
<220> FEATURE:
<223> OTHER INFORMATION: antisense sequence

<400> SEQUENCE: 34
ttagggatgg tgccg                                                15

<210> SEQ ID NO 35
<211> LENGTH: 15
<212> TYPE: DNA
<213> ORGANISM: Artificial Sequence
<220> FEATURE:
<223> OTHER INFORMATION: antisense sequence

<400> SEQUENCE: 35
ttggtttcca atcgg                                                15

<210> SEQ ID NO 36
<211> LENGTH: 15
<212> TYPE: DNA
<213> ORGANISM: Artificial Sequence
<220> FEATURE:
<223> OTHER INFORMATION: antisense sequence

<400> SEQUENCE: 36
aggggaggct cagtg                                                15
```

```
<210> SEQ ID NO 37
<211> LENGTH: 15
<212> TYPE: DNA
<213> ORGANISM: Artificial Sequence
<220> FEATURE:
<223> OTHER INFORMATION: antisense sequence

<400> SEQUENCE: 37
tcctcgctgc tggtg                                                       15

<210> SEQ ID NO 38
<211> LENGTH: 15
<212> TYPE: DNA
<213> ORGANISM: Artificial Sequence
<220> FEATURE:
<223> OTHER INFORMATION: antisense sequence

<400> SEQUENCE: 38
tcaaccagat ggtca                                                       15

<210> SEQ ID NO 39
<211> LENGTH: 15
<212> TYPE: DNA
<213> ORGANISM: Artificial Sequence
<220> FEATURE:
<223> OTHER INFORMATION: antisense sequence

<400> SEQUENCE: 39
ctgaatatca tgatt                                                       15

<210> SEQ ID NO 40
<211> LENGTH: 15
<212> TYPE: DNA
<213> ORGANISM: Artificial Sequence
<220> FEATURE:
<223> OTHER INFORMATION: antisense sequence

<400> SEQUENCE: 40
tgatgcttaa aagct                                                       15

<210> SEQ ID NO 41
<211> LENGTH: 15
<212> TYPE: DNA
<213> ORGANISM: Artificial Sequence
<220> FEATURE:
<223> OTHER INFORMATION: antisense sequence

<400> SEQUENCE: 41
tgtgaacata aattg                                                       15

<210> SEQ ID NO 42
<211> LENGTH: 15
<212> TYPE: DNA
<213> ORGANISM: Artificial Sequence
<220> FEATURE:
<223> OTHER INFORMATION: antisense sequence

<400> SEQUENCE: 42
ggtagtttag gaatt                                                       15

<210> SEQ ID NO 43
<211> LENGTH: 20
<212> TYPE: DNA
<213> ORGANISM: Artificial Sequence
<220> FEATURE:
<223> OTHER INFORMATION: control sequence
```

-continued

```
<400> SEQUENCE: 43
ttttaatcat attgttattc                                               20
```